US007569719B1

(12) United States Patent
McArdle et al.

(10) Patent No.: US 7,569,719 B1
(45) Date of Patent: Aug. 4, 2009

(54) METHOD OF PREPARING ELECTRON DEFICIENT OLEFINS

(75) Inventors: Ciaran B. McArdle, Dublin (IE); Ligang Zhao, Goettinger (DE)

(73) Assignee: Loctite (R&D) Limited, Dublin (IE)

( * ) Notice: Subject to any disclaimer, the term of this patent is extended or adjusted under 35 U.S.C. 154(b) by 0 days.

(21) Appl. No.: 11/877,700

(22) Filed: Oct. 24, 2007

Related U.S. Application Data

(60) Provisional application No. 60/862,816, filed on Oct. 25, 2006.

(51) Int. Cl.
    C07C 255/00 (2006.01)
(52) U.S. Cl. .................................... 558/462
(58) Field of Classification Search ............... None
    See application file for complete search history.

(56) References Cited

U.S. PATENT DOCUMENTS

| 2,363,464 | A | | 11/1944 | Senkus |
| 2,413,249 | A | | 12/1946 | Senkus |
| 2,413,250 | A | | 12/1946 | Senkus |
| 2,415,046 | A | | 1/1947 | Senkus |
| 2,582,128 | A | | 1/1952 | Hurwitz |
| 2,721,858 | A | | 10/1955 | Joyner et al. |
| 2,756,251 | A | | 7/1956 | Joyner et al. |
| 2,763,677 | A | | 9/1956 | Jeremias |
| 3,142,698 | A | | 7/1964 | Halpern et al. |
| 3,903,055 | A | | 9/1975 | Buck |
| 3,975,422 | A | | 8/1976 | Buck |
| 3,988,299 | A | | 10/1976 | Malofsky |
| 4,003,942 | A | | 1/1977 | Buck |
| 4,012,402 | A | | 3/1977 | Buck |
| 4,013,703 | A | | 3/1977 | Buck |
| 4,202,920 | A | | 5/1980 | Renner et al. |
| 4,364,876 | A | | 12/1982 | Kimura et al. |
| 4,512,357 | A | | 4/1985 | Earl |
| 4,556,700 | A | | 12/1985 | Harris et al. |
| 4,587,059 | A | | 5/1986 | Harth et al. |
| 4,622,414 | A | | 11/1986 | McKervey |
| 4,636,539 | A | | 1/1987 | Harris et al. |
| 4,695,615 | A | | 9/1987 | Leonard et al. |
| 4,718,966 | A | | 1/1988 | Harris et al. |
| 4,837,260 | A | | 6/1989 | Sato et al. |
| 4,855,461 | A | | 8/1989 | Harris |
| 4,876,045 | A | * | 10/1989 | Longo et al. ............... 552/526 |
| 4,906,317 | A | | 3/1990 | Liu |
| 5,142,098 | A | | 8/1992 | Bru-Magniez et al. |
| 5,288,794 | A | | 2/1994 | Attarwala |
| 5,306,752 | A | | 4/1994 | Attarwala |
| 5,312,864 | A | | 5/1994 | Wenz et al. |
| 5,328,944 | A | | 7/1994 | Attarwala et al. |
| 5,424,343 | A | | 6/1995 | Attarwala |
| 5,424,344 | A | | 6/1995 | Lewin |
| 5,455,369 | A | | 10/1995 | Meier et al. |
| 5,624,699 | A | | 4/1997 | Lang |
| 5,703,267 | A | | 12/1997 | Takahashi et al. |
| 5,744,642 | A | | 4/1998 | Lantzsch et al. |
| 6,093,780 | A | | 7/2000 | Attarwala |
| 6,096,848 | A | | 8/2000 | Gololobov et al. |
| 6,245,933 | B1 | | 6/2001 | Malofsky et al. |
| 6,291,544 | B1 | | 9/2001 | Kotzev |
| 6,531,460 | B1 | * | 3/2003 | Takenouchi et al. ......... 514/167 |
| 6,835,789 | B1 | | 12/2004 | Kneafsey et al. |
| 2006/0094833 | A1 | | 5/2006 | McDonnell et al. |

FOREIGN PATENT DOCUMENTS

| EP | 0 459 617 A1 | 12/1991 |
| WO | WO 94/15590 A1 | 7/1994 |
| WO | WO 95/32183 | 11/1995 |
| WO | WO 99/14206 A1 | 3/1999 |
| WO | WO 03/006225 A1 | 1/2003 |
| WO | WO 03/086605 A2 | 10/2003 |

OTHER PUBLICATIONS

Carl, J. Buck, Unequivocal Synthesis of Bis(2-Cyanoacrylate) Monomers, I. Via Anthracene Adducts, *Journal of Polymer Science, Polymer Chemistry Edition*, vol. 16, 2475-507 (1978).

G. Jones, "The Knoevenagle Condensation", *Organic Reactions*, vol. XV, 204, Wiley New York (1967).

F. Bigi et al., "Montmorillonite KSF as an Inorganic, Water Stable, and Reusable Catalyst for the Knoevenagel Synthesis of Coumarin-3-carboxylic Acids", *Journal Organic Chemistry*, vol. 64, 1033-35 (1999).

B. Green et al., Synthesis of Steroidal 16, 17-Fused Unsaturated δ-Lactones[1], *Journal Organic Chemistry*, vol. 50, 640-44 (1985).

P. Rao et al., "Zinc Chloride As A New Catalyst For Knoevenagel Condensation", *Tetrahedron Letters*, vol. 32, No. 41, 5821-22 (1991).

J. S. Yadav et al., "Phosphane-Catalyzed Knoevenagel Condensation: A Facile Synthesis of Cyanoacrylates and α-Cyanonitriles", *European Journal Organic Chemistry*, 546-51 (2004).

L. Tietze et al., Comprehensive Organic Synthesis, Pergamon Press, Oxford, vol. 2, Chapter 1.11, 341 (1991).

P. Laszlo, "Catalysis of Organic Reactions by Inorganic Solids", *Accounts of Chemical Research*, vol. 19, 121-27 (1986).

K. Kloestra et al., "Base and Acid Catalysis by the Alkali-containing MCM-41 Mesoporous Molecular Sieve", *Journal Chemical Soc. Chem. Commun.*, 1005-06 (1995).

P. Lednor et al., "The Use of a High Surface Area Silicon Oxynitride as a Solid, Basic Catalyst", *Journal Chemical Society, Chem. Commun.*, 1625-26 (1991).

F. Bigi et al., "A Revision of the Biginelli Reaction Under Solid Acid Catalysis. Solvent-free Synthesis Of Dihydropyrimidines Over Montmorillonite KSF", *Tetrahedron Letters*, vol. 40, 3456-68 (1999).

(Continued)

*Primary Examiner*—Paul A Zucker
(74) *Attorney, Agent, or Firm*—Steven C. Bauman

(57) ABSTRACT

This invention relates to processes for producing electron deficient olefins, such as 2-cyanoacrylates, using an iminium salt, and if desired contacting the reaction byproduct with alkali to generate an amine and separating that amine therefrom.

24 Claims, 1 Drawing Sheet

OTHER PUBLICATIONS

F. Bigi et al., "Clean synthesis in water: uncatalysed preparation of ylidenemalononitriles", *Green Chemistry*, vol. 2, 101-03 (2000).

R. Breslow, "Hydrophobic Effects on Simple Organic Reactions in Water", *Accounts of Chemical Research*, vol. 24, 159-64 (1991).

C. Li, "Organic Reactions in Aqueous Media—With a Focus on Carbon-Carbon Bond Formation", *Chemical Reviews*, vol. 93, 2023-35 (1993).

T. Welton, "Room Temperature Ionic Liquids, Solvents for Synthesis and Catalysis", *Chemical Reviews*, vol. 99, 2071-83 (1999).

D. Morrison et al., "Base-promoted reactions in ionic liquid solvents. The Knoevenagel and Robinson annulation reactions", *Tetrahderon Letters*, vol. 42, 6053-55 (2001).

Fraga-Dubreiul et al., "Grafted ionic liquid-phase-supported synthesis of small organic molecules", *Tetrahderon Letter*, vol. 42, 6097-6100 (2001).

M. Smietana et al., "Preparation of Silyl Enol Ethers Using (Bistrimethylsilyl)acetamide in Ionic Liquids", *Organic Letters*, vol. 3, No. 7, 1037-39 (2001).

Li et al., "n-Butyl Pyridinium Nitrate as a Reusale Ionic Liquid Medium for Knoevenagel Condensation", *Chinese Chemical Letters*, vol. 14, No. 5, 448-50 (2003).

J. Harjani et al., "Lewis acidic ionic liquids for the synthesis of electrophilic alkenes via the Knoevenagel condensation", *Tetrahedron Letters*, vol. 43, 1127-30 (2002).

Xu et al., "Knoevenagel condensation Reaction Catalyzed by Functionalized Ionic Liquid 1-(2-Hydroxyethyl)-3-methyl Imidazolium Chloride", *Chinese Journal of Organic Chemistry*, vol. 24(10), 1253-56 (2004).

Su et al., "Organic Reactions in Ionic Liquids: Knoevenagel Condensation Catalyzed by Ethylenediammonium Diacetate", *Synthesis 2003*, No. 4, 555-59 (2003).

Moehrle et al., "Aminomethylierung von 1,3-Diketonen", *Pharmazie*, vol. 40, 697-701 (1985).

J. March, "Reactions", *Advanced Organic Chemistry*, 3$^{rd}$ Edition, Wiley & Sons Inc., 417 (1985).

J. March, "Addition to Carbon-Hetero Multiple Bonds", *Advanced Organic Chemistry*, 3$^{rd}$ Edition, Wiley & Sons, 802-03 (1985).

M. B. Smith, *Organic Synthesis*, McGraw Hill International Chemistry Series, 1302 (1994).

Tehrani et al., "Product Class 8: Iminium Salts", *Science of Synthesis*, vol. 27, 313-48 (2004).

B. Hin et al., "Facile Synthesis of α-Substituted Acrylate Esters", *Journal of Organic Chemistry*, vol. 67, 7365-68 (2002).

Holy et al., "The Mannich Reaction-II Derivatization of Aldehydes and Ketones Using Dimethyl(methylene)ammonium Salts", *Tetrahedron Letters*, vol. 5, 613-19 (1979).

Bryson et al., "Preformed Mannich Salts: A Facile Preparation of Dimethyl(methylene)ammonium Iodide", *Journal of Organic Chemistry*, vol. 45, 524-25 (1980).

J. March, "The Pinacol Rearrangement", *Advanced Organic Chemistry*, 3$^{rd}$ Edition, Wiley & Sons, 963-64 (1985).

J. March, "Free-Radical Substitution", *Advanced Organic Chemistry*, 3$^{rd}$ Edition, Wiley & Sons, 642 (1985).

Jahn et al., "A Novel and Simple Method for the Preparation of Iminium Salts", *Tetrahderon Letters*, vol. 34, No. 37, 5863-66 (1993).

R. J. Vijin et al., Synthesis, 573 (1994).

Davis, "Chemistry Letters", vol. 33, Issue 9, 1072-77 (2004).

Davis et al., "Ionic Liquids in Synthesis", P. Wasserscheld and T. Welton, eds., Wiley-VCH Verlag GmbH & Co., KGaA, Chapter 2 (2002).

M.G. Djamali, P. Burba, K.H. Lieser, "Synthese und Eigenschaften eines Celluloseaustauschers mit Diaminodibenzo-18-Krone-6 als Ankergruppe", *Die Angewandte Makromolecular Chemie*, vol. 92, 145-54 (1980).

K. Babic, "Reactive and Functional Polymers", vol. 66, 1494-1505 (2006).

Trumbo et al., "Copolymerization Behavior of 3-Isopropenyl-α,α-Dimethylbenzylamine and Preliminary Evaluation of the Copolymers In Thermoset Coatings", *Journal of Applied Polymer Science*, vol. 82, 1030-39 (2001).

T. Giesenberg et al., "Synthesis and Functionalization of a New Kind of Silica Particle," *Agnew. Chem. Int. Ed.*, 43, 5697-5700 (2004).

Zhang et al., "An Investigation of Knoevenagel condensation reaction in microreactors using a new zeolite catalyst", *Applied Catalysis A: General* 261, 109-118 (2004).

Mehnert et al., "Chemical Communications", 3010 (2002).

Lee and Lee, "Bulletin of the Korean Chemical Society", vol. 25, Issue 10, 1531-37 (2004).

H. R. Snyder and W. E. Hamlin, "Alkylation of Nitroparaffins with Amines and Their Derivatives", *Journal of American Chemical Society*, vol. 72, 5082-85 (1950).

H. G. Johnson, "Reaction of Aliphatic Amines with Formaldehyde and Nitroparaffins. II. Secondary Amines", *Journal of American Chemical Society*, vol. 68, 12-14 (1946).

M. Semkus, "Journal of the American Chemical Society", vol. 68, 10-12 (1946).

Sarac, "Progress in Polymer Science", vol. 24, 1149-1201 (1999).

Brough et al., "Pyrimidinyl Nitronyl Nitroxides", *Chemical European Journal*, vol. 12, 5134 (2006).

Zhou et al., *J. Polymn. Sci., Part A Polym. Chem. Ed.*, 29, 1097 (1991).

Mehrotra et al., "Journal of Organometalic Chemistry", vol. 24, 611-21 (1970).

Son et al., "Synthesis of Hexahydro 3,3,5,5,7-pentaalkyl-2H-1,4-diazepin-2-ones from 1,3-Diamines And Ketones", *J. Org. Chem.*, vol. 46, 323 (1981).

Senkus, Acetals of Nitro Alcohols and Corresponding Amino Acetals, *J. Amer. Chem. Soc.*, vol. 69, 1380-81 (1947).

Renner et al., "Cure of Epoxy Resins with Esters of Cyanoacrylic Acid", *Journal of Polymer Science: Polymer Chemistry Edition*, vol. 23, 2341 (1985).

Kennedy et al., "Macromers by Carbocationic Polymerization. X. Synthesis, Characterization, and Polymerizability of Cyanoacrylate-Capped Polyisobufylenes", *Journal of Macromolecular Science, Part A*, 28:2, 209-24 (1991).

Khrustalev et al., "Synthesis and X-ray structural study of 1-adamantylmethy 2-cyanoacrylatel And 1,10-decanediol bis-2 cyanoacrylate", *Russian Chemical Bulletin*, vol. 45, No. 9, 2172 (1996).

Y. Gololobov et al., "A novel approach to the synthesis of bis(2-cyanoacrylates)", *Russian Chemical Bulletin*, vol. 42, No. 5, 961 (1993).

Y. Gololobov et al., "Synthesis of bis(2-cyanoacrylates) from 2-cyanoacryloyl chloride and 2-butene-and-2-butyne-1,4-diols", *Russian Chemical Bulletin*, vol. 44, No. 4, 760 (1995).

J.-L. De Keyser et al., "A Versatile and Convenient Multigram Synthesis of Methylidenemalonic Acid Diesters", *J. Org. Chem.*, vol. 53, 4859 (1988).

Vijayalakshmi et al., "Alkyl and substituted alkyl 2-cyanoacrylates. Part I. Synthesis and Properties", *J. Adhesion Science Technology*, vol. 4, No. 9, 733 (1990).

Guseva et al., "Organic Chemistry. Synthesis of functionality substituted cyanoacetates." *Russian Chemical Bulletin*, vol. 42, No. 3, 478 (1993).

Guseva et al., "Organic Chemistry", *Russian Chemical Bulletin*, vol. 43, No. 4, 595 (1995).

Gololobov and Gruber, Russian Chemical Review, vol. 66, Issue 11, 953 (1997).

Senchenya et al., "Silicon-containing esters of α-cyanoacrylic acid: synthesis and properties" *Russian Chemical Bulletin*, vol. 42, No. 5, 909 (1993).

Bowie, J. H. et al., "Tetrahderon", vol. 23, 305-20 (1967).

J. S. Norwick et al., J. Org. Chem., 57(28), 7364-66 (1992).

\* cited by examiner

Reactions A, B, and C respectively

METHOD OF PREPARING ELECTRON DEFICIENT OLEFINS

BACKGROUND OF THE INVENTION

1. Field of the Invention

This invention relates to processes for producing electron deficient olefins, such as 2-cyanoacrylates, using an iminium salt, and if desired contacting the reaction byproduct with alkali to generate an amine and separating that amine therefrom.

2. Brief Description of Related Technology

Cyanoacrylate adhesives are known for their fast adhesion and ability to bond a wide variety of substrates. They are marketed as "super glue" type adhesives. They are useful as an all-purpose adhesive since they are a single component adhesive, very economical as only a small amount will do, and generally do not require any equipment to effectuate curing.

Traditionally, cyanoacrylate monomers have been produced by way of a Knoevenagel condensation reaction between a formaldehyde precursor, such as paraformaldehyde, and an alkyl cyanoacetate with a basic catalyst. During the reaction, cyanoacrylate monomer forms and polymerises in situ to a prepolymer. The prepolymer that is subsequently thermally cracked or depolymerised, yielding cyanoacrylate monomer. This approach has remained essentially the same over time, though various improvements and variants have been introduced. See e.g. U.S. Pat. Nos. 6,245,933, 5,624, 699, 4,364,876, 2,721,858, 2,763,677 and 2,756,251.

In U.S. Pat. No. 3,142,698, the synthesis of difunctional cyanoacrylates using a Knoevenagel condensation reaction is described. However, the ability to thermally depolymerise the resulting, now crosslinked, prepolymer in a reliable and reproducible manner to produce pure difunctional monomers in high yields is questionable [see J. Buck, *J. Polym. Sci., Polym. Chem. Ed.*, 16, 2475-2507 (1978), and U.S. Pat. Nos. 3,975,422, 3,903,055, 4,003,942, 4,012,402, and 4,013,703].

A variety of other processes for producing cyanoacrylate monomers are known, and some of which described below.

U.S. Pat. No. 5,703,267 defines a process for producing a 2-cyanoacrylic acid which comprises subjecting a 2-cyanoacrylate and an organic acid to a transesterification reaction.

U.S. Pat. No. 5,455,369 defines an improvement in a process for preparing methyl cyanoacrylate, in which methyl cyanoacetate is reacted with formaldehyde to form a polymer that is then depolymerized to the monomeric product, and in which the purity of yield is 96% or better. The improvement of the '369 patent is reported to be conducting the process in a poly(ethylene glycol) diacetate, dipropionate, or dibutyrate, having a number average molecular weight of 200-400, as the solvent.

U.S. Pat. No. 6,096,848 defines a process for the production of a biscyanoacrylate, which comprises the steps of esterifying a 2-cyanoacrylic acid or transesterifying an alkyl ester thereof to obtain a reaction mixture; and fractionally crystallizing the reaction mixture to obtain the biscyanoacrylate.

U.S. Pat. No. 4,587,059 defines a process for the preparation of monomeric 2-cyanoacrylates comprising the steps of (a) reacting (i) a 2,4-dicyanoglutarate with (ii) formaldehyde, cyclic or linear polymers of formaldehyde, or a mixture thereof, in the presence of between about 0.5 and about 5 mols of water per mol of 2,4-dicyanoglutarate, at an acid pH of about 3 to slightly less than 7, and at a temperature of about 70 about 140, to form an oligomeric intermediate product, and (b) removing water that is present from step (a) and thermolyzing the oligomeric intermediate product for a period of time sufficient to effect its conversion to monomeric 2-cyanoacrylates.

Commercial production of cyanoacrylate monomers ordinarily relies on the depolymerisation of a prepolymer formed under Knoevenagel condensation reaction conditions, as noted above. Still today the Knoevenagel condensation reaction is believed to remain the most efficient and prevalent commercial method for producing high yields of monofunctional cyanoacrylates. Nevertheless, it would be desirable to not have to resort to thermally induced depolymerisation of a prepolymer produced by the Knoevenagel condensation reaction. This prospect may also enable facile access to highly useful difunctional monomers, such as so-called bis-cyanoacrylates or hybrid materials of cyanoacrylate and other polymerisable or reactive functionality.

The Knoevenagel condensation reaction is well known not only for its usefulness in the manufacture of cyanoacrylates, but also (and perhaps more so) for its immense potential generally in the synthesis of electrophilic olefins from active methylene and carbonyl compounds [G. Jones, *Organic Reactions*, Vol. XV, 204, Wiley, New York (1967)]. A wide range of catalysts have been employed in carrying out this reaction, each affording variable yields of olefins. More recently, heterogeneous catalysts have been used, many of which include inorganic materials such as clays and zeolites [F. Bigi et al., *J. Org. Chem.*, 64, 1033 (1999)]. These materials are environmentally benign and have been used because they are ditopic in nature, some containing both acidic and basic sites, while others are solely acidic or solely basic. Some Lewis acid catalysts have also been employed in the Knoevenagel condensation reaction [B. Green et al., *J. Org. Chem.*, 50, 640 (1985); P. Rao et al., *Tett. Lett.*, 32, 5821 (1991)]. Since bases are generally active nucleophiles and cyanoacrylate monomers are highly susceptible to initiation of polymerisation by active nucleophiles, it is not possible to exploit base catalysed Knoevenagel synthesis of cyanoacrylate monomer without polymerisation occurring. And while acid catalysed Knoevenagel condensation reactions to form cyanopentadienoate monomers (related to cyanoacrylates) are known (see e.g. U.S. Pat. No. 6,291,544), these routes do not lead to the direct synthesis of cyanoacrylate monomers per se.

The Knoevenagel condensation reaction also liberates water during the condensation of aldehydes with reactive methylene compounds, and neutral and basic water is well known to initiate polymerisation of cyanoacrylate monomers.

Recently, J. S. Yadav et al., "Phosphane-Catalyzed Knoevenagel Condensation: A Facile Synthesis of α-Cyanoacrylates and α-Cyanonitriles", *Eur. J. Org. Chem.*, 546-551 (2004) reports of the use of triphenylphosphane [sic, triphenylphosphine] as a catalyst for the Knoevenagel condensation of aldehydes with acidic methylene compounds, such as ethyl cyanoacetate and malonitrile, to afford substituted olefins in an efficient manner under mild and solvent-free conditions. Triphenyphosphine is a known initiator for the polymerization of 2-cyanoacrylates.

Absent from the published literature is the use of iminium salts in the preparation of electron deficient olefins, such as 2-cyanoacrylates.

Iminium salts are salts of imines that are in turn reaction products of carbonyl containing compounds and amines. General methods of simple imine formation are described for instance in R. J. Vijin et al., *Synthesis*, 573 (1994) and U.S. Pat. Nos. 2,582,128 and 5,744,642.

In International Patent Publication No. WO 2003/06225 A1 assigned to BASF Aktiengesellschaft, Lugwigshafen, Germany, ionic liquid precursors such as methyl imidazole are used as solvents and acid scavengers in specific reactions that are known to expel acid byproducts. When these ionic liquid precursors become protonated by the acid expelled during a chemical reaction, such as an esterification of an acid chloride for example, a liquid salt (methyl imidazolium hydrochloride, for example) forms and subsequently phase separates from the reaction products. That phase separated liquid salt is readily removable and may be treated by base to recycle the original ionic liquid precursor scavenger (methyl imidazole). The ease of removability of a liquid salt byproducts and the recylability of the byproduct makes this an attractive and important commercial process (so-called BASIL™ process, Biphasic Acid Scavenging Ionic Liquid).

Standard practice to those skilled in the art of organic chemistry is the use of liquid amines, such as triethylamine, as acid scavengers to produce solid quaternary salts. However, these solid quaternary salts are oftentimes difficult and time consuming to separate off from the reaction mixture and are known to cause stirring problems due to thickening of the reaction mixtures, particularly on large reaction scales.

SUMMARY OF THE INVENTION

Unlike the state of the technology, the present invention provides a direct or substantially "crackless" synthesis of electron deficient olefins, such as 2-cyanoacrylate ester monomers using an iminium salt. The synthesis hereby provided may be catalysed or uncatalysed. And the synthesis permits the recycling and/or recovery of certain starting material reagents to permit a continuous process, if desired, which is generally more efficient than known syntheses of electron deficient olefins.

The present invention provides a process for the preparation of a reactive electron deficient olefin. In one aspect, the invention includes the steps of:

(a) providing an iminium salt and a compound containing a methylene linkage having at least one electron withdrawing substituent attached thereto, where the electron withdrawing substituent is selected from nitrile, carboxylic acids, carboxylic esters, sulphonic acids, ketones or nitro;

(b) reacting the iminium salt and the compound under appropriate conditions and for a time sufficient to yield a reactive electron deficient olefin and an ammonium salt, such as a quaternary ammonium salt;

(c) separating the so formed reactive electron deficient olefin to yield the reactive electron deficient olefin, desirably substantially free from the iminium salt, the compound, ammonium salt or combinations thereof;

(d) contacting that which remains from step (c) with alkali to generate an amine;

(e) optionally separating the amine formed in step (d); and (f) optionally contacting the amine formed in step (d) with a carbonyl-containing compound under appropriate conditions and for a time sufficient to yield an imine; and (g) optionally contacting the imine formed in step (f) with an acid under appropriate conditions and for a time sufficient to yield an iminium salt.

In another aspect, the invention provides a process for the preparation of a 2-cyanoacrylate ester. The steps of this process include (a) providing as reactants formaldehyde (or a source thereof) having the structure R—CH═O, where R is hydrogen or vinyl, and an amine, such as a primary amine, to form an imine;

(b) reacting the imine from step (a) under appropriate conditions and for a time sufficient to yield an iminium salt;

(c) providing an alkyl cyanoacetate and reacting the iminium salt from step (b) therewith;

(d) separating from the mixture the so-formed 2-cyanoacrylate ester to yield 2-cyanoacrylate ester, desirably substantially free from reactants, such as the iminium salt, the alkyl cyanoacetate and combinations thereof;

(e) contacting that which remains from step (d) with alkali to generate an amine; and (f) optionally separating from the mixture an amine formed in step (e); and (g) optionally contacting the amine separated in step (f) with a carbonyl-containing compound under appropriate conditions and for a time sufficient to yield an imine; and (h) optionally contacting the imine formed in step (g) with an acid under appropriate conditions and for a time sufficient to yield an iminium salt.

In either aspect, the process may be conducted with or without added catalyst. When a catalyst is added, desirably the catalyst should be one that is not a solely basic nucleophile. Thus, an acidic system would be preferred and a ditropic system may be used, as well.

By the present invention, a variation of the BASIL™ process is used such that the reaction substrate itself, e.g., an imine, is receptive to added, rather than expelled acid, and no specific additional acid scavengers or precursor thereof, is added. When various solvent systems and/or acids are used with reaction substrates, such as imines, a phase separation occurs, after which additional reagents may be added, such as an iminium salt, which may be added as a solution. The reaction is capable of operating to produce a high conversion of reactive electron deficient olefin, such as 2-cyanoacrylate ester, under appropriate conditions (such as 70° C. in acids or acidified organic solvents for periods of 1-3hours). See FIG. 1. And if starting material reagents and/or reaction byproducts are sought to be recovered and/or recycled, the steps of the processes of the various aspects may be repeated.

The electron deficient olefin, such as ethyl cyanoacrylate, may be found in the lower acidified organic solvent phase with some unreacted reagent(s) (e.g., unconverted ethyl cyanoacetate) and the majority of the byproducts (acidified mixtures of quaternary ammonium salts) may be found in the upper liquid phase which may be removed and treated to recover the initial amine that forms the imine substrate. The biphasic liquid-liquid separation makes separation facile. Further iminium reagent(s) may be added to the lower phase and the reaction may continue to deliver a higher conversion of electron deficient olefin.

DETAILED DESCRIPTION OF THE INVENTION

Figure 1:
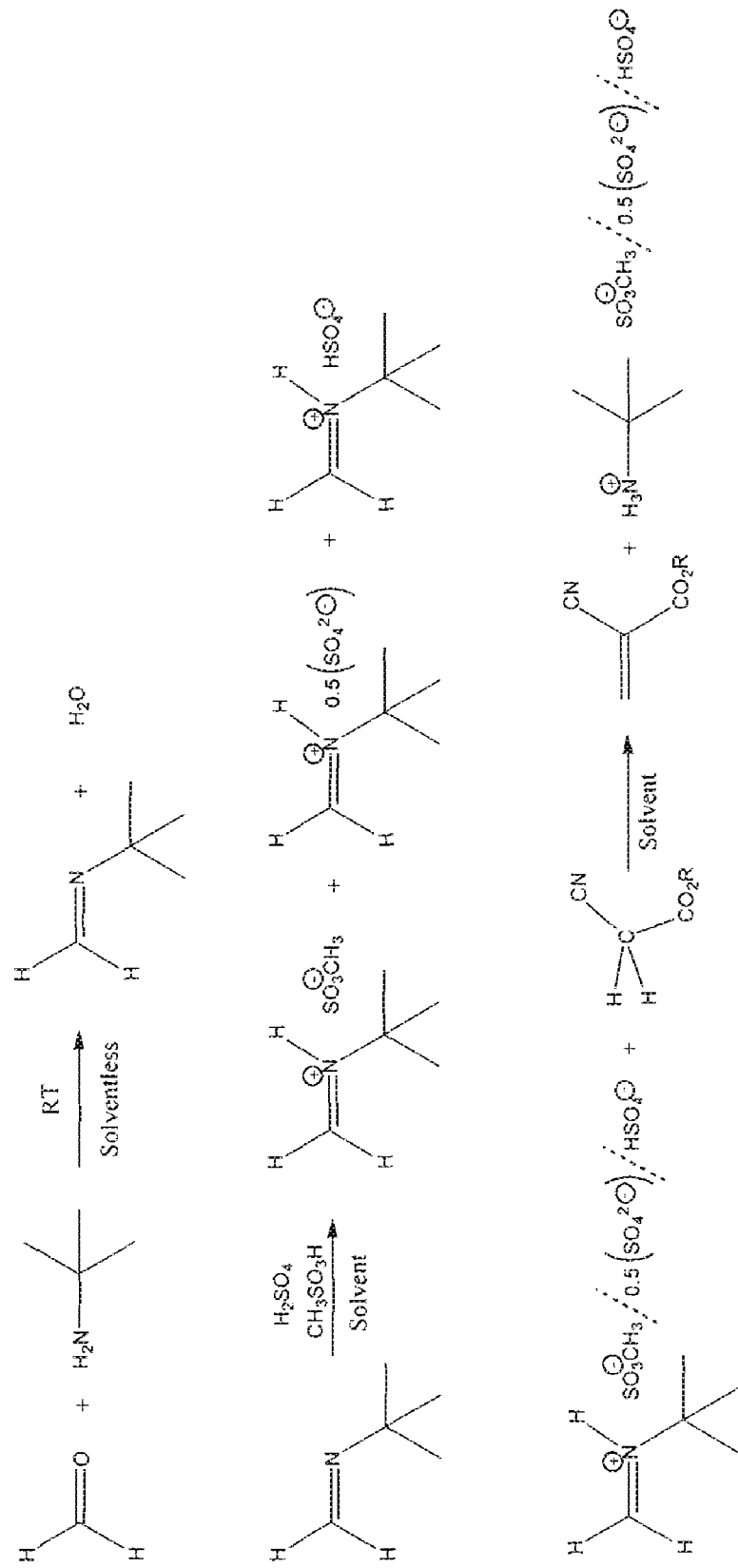
FIG. 1 depicts a synthetic scheme according to the present invention.

As noted above, the present invention provides a process for the preparation of a reactive electron deficient olefin. In one aspect, the invention includes the steps of:

(a) providing an iminium salt and a compound containing a methylene linkage having at least one electron withdrawing substituent attached thereto, where the electron withdrawing substituent is selected from nitrile, carboxylic acids, carboxylic esters, sulphonic acids, ketones or nitro;

(b) reacting the iminium salt and the compound under appropriate conditions and for a time sufficient to yield a reactive electron deficient olefin and an ammonium salt, such as a quaternary ammonium salt;

(c) separating from the mixture the so formed reactive electron deficient olefin to yield the reactive electron deficient olefin, desirably substantially free from the iminium salt, the compound, the ammonium salt or combinations thereof;

(d) contacting that which remains from step (c) with alkali to generate an amine;

(e) optionally separating the amine formed in step (d); and (f) optionally contacting the amine formed in step (d) with a carbonyl-containing compound under appropriate conditions and for a time sufficient to yield an imine; and (g) optionally contacting the imine formed in step (f) with an acid under appropriate conditions and for a time sufficient to yield an iminium salt.

In another aspect, the invention provides a process for the preparation of a 2-cyanoacrylate ester. The steps of this process include (a) providing as reactants formaldehyde (or a source thereof) having the structure R—CH═O, where R is hydrogen or vinyl, and an amine, such as a primary amine, to form an imine;

(b) reacting the imine from step (a) under appropriate conditions and for a time sufficient to yield an iminium salt;

(c) providing an alkyl cyanoacetate and reacting the iminium salt from step (b) therewith;

(d) separating from the mixture the so-formed 2-cyanoacrylate ester to yield 2-cyanoacrylate ester, desirably substantially free from the iminium salt and the alkyl cyanoacetate;

(e) contacting that which remains from step (d) with alkali to generate an amine; and (f) optionally separating from the mixture an amine formed in step (e); and (g) optionally contacting the amine separated in step (f) with a carbonyl-containing compound under appropriate conditions and for a time sufficient to yield an imine; and (h) optionally contacting the imine formed in step (g) with an acid under appropriate conditions and for a time sufficient to yield an iminium salt.

Of course, the invention also provides a process for using iminium salts to prepare reactive electron deficient olefins.

Iminium salts (also in the past referred to as immonium salts) may be methanimimium salts, derived from formaldehyde, ternary imminium salts derived from aldehydes, eg, acrolein, and quaternary imminium salts derived from ketones [Abbaspour Tehrani and De Kimpe, Science of Synthesis, 27, 313 (2004), and references cited therein].

In any of these aspects, the process may be conducted with or without added catalyst, as noted above. And when a catalyst is added, desirably the catalyst should be one that is not a solely basic nucleophile. Thus, an acidic system would be preferred and a ditropic system may be used, as well.

Reference to FIG. 1 may be useful to appreciate further the present invention, which is described in more detail below and in the Examples section.

Thus, as an initial reactant in the inventive processes are aldehyde compounds having the structure R—CH═O, where R is hydrogen or vinyl. The aldehyde compound may be an aldehyde itself or a source of an aldehyde, such as one that yields an aldehyde like formaldehyde under reaction conditions. The aldehyde compound in a desirable embodiment includes formaldehyde (or a source thereof, such as paraformaldehyde), formalin, or 1,3,5-trioxane, or vinyl aldehydes, such as acrolein.

As a reactant with such an aldehyde is an amine, such as a primary amine like aniline, N-methylamine, N-propylamine or hydroxylamine, its ethers and salts thereof. Desirably, when a primary amine is used, the primary amine should be one with some degree of steric hinderance, such as tertiary butyl amine. (See FIG. 1, A.)

Secondary amines are not used directly in the formation of imminium salts, rather normal salts of secondary amines such as dimethylamine, pyrrolidine, morpholine, and the like are used to react with the carbonyl compound to produce imminium salts, also know as Mannich bases [Abbaspour Tehrani and De Kimpe, Science of Synthesis, 27, 313 (2004), and references cited therein, Jahn and Schroth, Tett. Lett., 34(37), 5863 (1993)].

Imines per se are produced by reaction of a carbonyl compound (e.g., in an aldehyde or ketone) and an amine, such as a primary amine, where water is removed from the reaction. Thus, secondary amines (possessing only one hydrogen as opposed to two hydrogens as on a primary amine) do not produce imines directly (but rather can produce imines indirectly as discussed below). The reaction of primary amine with carbonyl compound is well known and can be a facile, high yielding reaction that may be conducted on a commercial scale (in the case of primary amines, see U.S. Pat. Nos. 2,582,128 and 5,744,642). The so-formed imines from primary amines may be converted into iminium salts by contacting them with an acidic species, such as trifluoroacetic acid, acetic acid, sulphuric acid, methane sulfonic acid, or camphor sulfonic acid [see e.g. J. March at 802, and references cited therein; see also M. B. Smith, Organic Synthesis, McGraw Hill International, Chemistry Series, 1302 (1994) and references cited therein]. (See also FIG. 1, B.)

Iminium salts can also be formed from carbonyl compounds and a secondary amine, though in salt form, or by reaction of chloromethyl ethers with N-(trimethylsilyl) amines. See e.g. Jahn and Schroth, Tett. Lett., 34(37), 5863 (1993) and Abbaspour Tehrani and De Kimpe, Science of Synthesis, 27, 313 (2004), and references cited therein.

Some iminium salts are available commercially, such as Eschenmoser's salt that is available from The Aldrich Chemical Co. Eschenmoser's salt has been used in the synthesis of acrylates [see e.g. Hin, B., Majer, P., Tsukamoto, T., J. Org. Chem., 67, 7365 (2002)] and in Mannich reactions [Holy et al, Tetrahedron, 35, 613 (1979), and Bryson et al, J. Org Chem., 45, 524 (1980)].

Indeed, imines and iminium salts may even be formed without the use of a carbonyl compound at the outset. Thus, for example, Jahn and Schroth have described a method for the preparation of iminium salts, Tett. Lett., 34 (37), 5863 (1993), in which alpha-chloroethers may be used to form "Mannich reagents", which are iminium salts. Oxidation of amines can lead to imines, as well, and hence iminium salts.

The imine salt may be represented as follows:

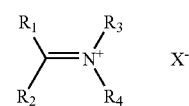

where $R_1$, $R_2$, $R_3$ are each H and $R_4$ is an alkyl, such tertiary-butyl; X is $SO_3CH_3$, for example, 0.5 ($SO_4^{2-}$), $HSO_4^-$ or mixtures thereof, if a mixture of the corresponding acids has been used during the protonation of the imine. Examples of imines formed therefrom thus include N-methylidene-tertiary butylamine, N-methylideneaniline, N-methylidenemethylamine and N-methylidenepropylamine.

Alternatively, or more specifically, for the imine salt above $R_1$, $R_2$, $R_3$, $R_4$ and X may be chosen as follows:

A. $R_1$ is $CH_2$=CH, $R_2$ and $R_3$ are each H, $R_4$ is alkyl, such as tert-butyl, and X is $SO_3CH_3$, 0.5 ($SO_4^{2-}$) or mixtures of both anions, $PF_6$, $BF_4$, $AsF_6$, $SbF_6$, $Tf_2N$, $(CN)_2N$, triflate, camphorsulfonate, saccharinate, acesulfamate, $MF_6$, where M is Nb, Ta, nitrate, $CF_3CO_2$, halide, phosphate, or perchlorate;

B. $R_1$ and $R_2$ are each $CH_2$=CH, $R_3$ is H, $R_4$ is alkyl, such as tert-butyl, and X is $SO_3CH_3$, 0.5 ($SO_4^{2-}$), mixtures of both anions, $PF_6$, $BF_4$, $AsF_6$, $SbF_6$, $Tf_2N$, $(CN)_2N$, triflate, camphorsulfonate, saccharinate, acesulfamate, $MF_6$, where M is Nb, Ta, nitrate, $CF_3CO_2$, halide, phosphate, or perchlorate;

C. $R_1$ is H or $CH_2$=CH, $R_2$ is $R_1C$=$N^+(R_3)$ $(R_4)X^-$, $R_3$ is H, $R_4$ is alkyl, such as tert-butyl, and X is $SO_3CH_3$, 0.5 ($SO_4^{2-}$) or mixtures of both anions, $PF_6$, $BF_4$, $AsF_6$, $SbF_6$, $Tf_2N$, $(CN)_2N$, triflate, camphorsulfonate, saccharinate, acesulfamate, $MF_6$, where M is Nb, Ta, nitrate, $CF_3CO_2$, halide, phosphate, or perchlorate;

D. $R_1$ and $R_2$ are each independently selected from H or $CH_2$=CH, $R_3$ and $R_4$ are each independently selected from alkyl groups, such as methyl or tert-butyl, or aromatic groups, X is $SO_3CH_3$ 0.5 ($SO_4^{2-}$) or mixtures of both anions, $PF_6$, $BF_4$, $AsF_6$, $SbF_6$, $Tf_2N$, $(CN)_2N$, triflate, camphorsulfonate, saccharinate, acesulfamate, or $MF_6$, where M is Nb, Ta, nitrate, $CF_3CO_2$, halide, phosphate, or perchlorate;

E. $R_1$ is H or $CH_2$=CH, $R_2$ is $R_1C$=$N^+(R_3)$ $(R_4)X^-$, $R_3$ and $R_4$ are each independently selected from alkyl groups, such as methyl or tert-butyl, or aromatic groups, X is $SO_3CH_3$ 0.5 ($SO_4^{2-}$) or mixtures of both anions, $PF_6$, $BF_4$, $AsF_6$, $SbF_6$, $Tf_2N$, $(CN)_2N$, triflate, camphorsulfonate, saccharinate, acesulfamate, or $MF_6$, where M is Nb, Ta, nitrate, $CF_3CO_2$, halide, phosphate, or perchlorate;

F. $R_1$ and $R_2$ are each independently selected from H or $CH_2$=CH, $R_3$ is H, $R_4$ is OH, OR, where R is an alkyl group, aromatic group, or a carboxy group, and X is $SO_3CH_3$, 0.5 ($SO_4^{2-}$) or mixtures of both anions, $PF_6$, $BF_4$, $AsF_6$, $SbF_6$, $Tf_2N$, $(CN)_2N$, triflate, camphorsulfonate, saccharinate, acesulfamate, or $MF_6$, where M is Nb, Ta, nitrate, $CF_3CO_2$, halide, phosphate, or perchlorate;

G. $R_1$ is selected from H or $CH_2$=CH, $R_2$ is $R_1C$=$N^+(R_3)$ $(R_4)X^-$, $R_3$ is H, $R_4$ is OH, OR, where R is an alkyl group, aromatic group, or a carboxy group, and X is $SO_3CH_3$, 0.5 ($SO_4^{2-}$) or mixtures of both anions, $PF_6$, $BF_4$, $AsF_6$, $SbF_6$, $Tf_2N$, $(CN)_2N$, triflate, camphorsulfonate, saccharinate, acesulfamate, or $MF_6$, where M is Nb, Ta, nitrate, $CF_3CO_2$, halide, phosphate, or perchlorate; or H. $R_1$ and $R_2$ are each is selected from H or $CH_2$=CH, $R_3$ is selected from alkyl groups or aromatic groups, $R_4$ is selected from OH, OR, where R is an alkyl group, aromatic group, or a carboxy group, X is selected from $SO_3CH_3$, 0.5 ($SO_4^{2-}$) or mixtures of both anions, $PF_6$, $BF_4$, $AsF_6$, $SbF_6$, $Tf_2N$, $(CN)_2$, triflate, camphorsulfonate, saccharinate, acesulfamate, or $MF_6$, when M is Nb, Ta, nitrate, $CF_3CO_2$, halide, phosphate, or perchlorate.

The so-formed iminium salts are then reacted with compounds containing a methylene linkage having at least one electron withdrawing substituent attached thereto. In these compounds, the electron withdrawing substituent is selected from nitrile, carboxylic acids, carboxylic esters, sulphonic acids, ketones or nitro. In a desirable embodiment, these compounds have two or more electron withdrawing substituents, which may be the same or different, such as nitrile and carboxylic acid ester—in this case, a cyanoacrylate. (See FIG. 1, C.)

Representative examples of these compounds include malononitrile, malonic acid and its esters, ethyl nitroacetate, cyanoacetic acid and its esters, 4-cyclopentene-1,3-dione, cyclopentane-1,3-dione, 4-cyclohexene-1,3-dione, cyclohexane-1,3-dione, 2,2-dimethyl-1,3-dioxane-4,6-dione (Meldrum's acid), and tetronic acid, some of which are commercially available for instance from The Aldrich Chemical Co. A particularly desirable example is ethyl cyanoacetate.

The structures below illustrate the olefinic products that would result from a reaction involving iminium salts with examples of the aforementioned methylene compounds.

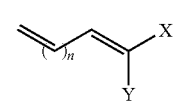

I

Here, when a source of formaldehyde is used, n is 0 in structure I and a methylenic compound results with X and Y being nitrile, carboxylic acid, carboxylic acid esters; X being nitro and Y being carboxylic acid ester; or X being nitrile and Y being carboxylic acid ester, the latter combination giving rise to 2-cyanoacrylates using alkyl cyanoacetates as a substrate, for example. When acrolein is used, n is 1 and the same combinations of X and Y can apply in structure I.

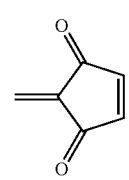

II

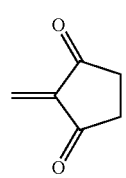

III

When a source of formaldehyde is used, structures II and III would result when cyclopentene diones, cyclohexene diones, cyclopentane diones or cyclohexane diones are used. When acrolein is used, the methylene bond would be conjugated to another alkene group (by analogy to structure I above).

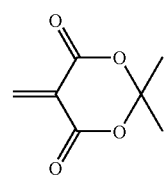

IV

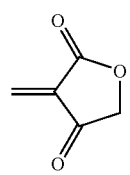

V

When a source of formaldehyde is used, structures IV and V may result when Meldrum's acid and tetronic acid are used.

When acrolein is used, the methylene bond again would be conjugated to another alkene group (by analogy to structure I above).

The electron deficient olefin so formed by the inventive processes may be a variety of olefins having at least one electron withdrawing group attached thereto. In a desirable embodiment, as noted above with respect to the second reactant, the electron deficient olefin so formed will have two or more electron withdrawing groups attached thereto, which may be the same or different. Particularly desirable products have two electron withdrawing groups attached thereto which are different, such as 2-cyanoacrylate esters, where the electron withdrawing groups are the cyano group and the ester group.

Representative examples of 2-cyanoacrylate esters so formed by the inventive processes include methyl, ethyl, n-propyl, i-propyl, propargyl, n-butyl, i-butyl, n-pentyl, n-hexyl, 2-ethylhexyl, n-octyl, n-nonyl, oxononyl, n-decyl, n-dodecyl, allyl, ethynyl, 2-butenyl, cyclohexyl, phenyl, phenethyl, tetrahydrofurfuryl, chloroethyl, 2,2,2-trifluoroethyl, hexafluoroisopropyl, methoxymethyl, methoxyethyl, methoxybutyl, ethoxyethyl, propoxyethyl, butoxymethyl, butoxyethyl and dimethyl siloxane esters of 2-cyanoacrylic acid.

The electron deficient olefin may also be a compound having one end terminating with a cyanoacrylate, cyanopentadienoate, or alkylene derived from dimalonate and another end terminating with a group selected from the group consisting of branched and unbranched alkyl esters, esters containing aromatics and heterocyclic nuclei, acrylates, cyanoacrylates, siloxanes, blocked and unblocked isocyanates, anhydrides, silanes, vinyls, and acetylenes.

Of course, salt is also formed. (See FIG. 1, C.)

The reaction of the inventive process may proceed with or without heating or cooling, depending of course on the specific reactants and the scale of the reaction.

Decomposition of the source of formaldehyde, e.g., paraformaldehyde, may occur under gentle heating up to a temperature of 70°C., to liberate formaldehyde in situ in the reaction medium. The temperature may be reached through an external heating element or internally by means of the exotherm that may be generated depending on the identity of the reactants. The temperature of the reaction should be controlled however to accommodate any such exothermic processes.

The time of reaction may be monitored by reference to the formation of the desired electron deficient olefin product. A $^1$H NMR spectrometer is a particularly useful tool in this regard. The time of reaction may be as little as 30 minutes, for instance, or longer or shorter for that matter depending again on the identity of the specific reactants, the scale of the reaction and whether heat is added to the reaction conditions.

Once formed, the electron deficient olefin product may be isolated by distillation under vacuum out of the reaction mixture following solvent evaporation, or by freezing it in a solid form and separating off the liquid phase. The former method is particularly desirable in the case of 2-cyanoacrylates (particularly their lower esters), which are relatively volatile.

The electron deficient olefin so formed by the inventive processes may be stabilized during the synthesis and/or isolation procedure, and also in the isolated product to improve its shelf life. Suitable stabilizers include free radical stabilizers and acidic stabilizers.

For example, free radical stabilizers include hydroquinone, pyrocatechol, resorcinol or derivatives thereof, such as hydroquinone monoethyl ether, or phenols, such as di-t-butylphenol or 2,6-di-t-butyl-p-cresol, 2,2'-methylene-bis-(4-methyl-6-t-butylphenol), bisphenol A, dihydroxydiphenylmethane, and styrenized phenols.

For example, acidic stabilizers include sulfuric acid, hydrochloric acid, sulfonic acids, such as methane, ethane or higher sulfonic acids, p-toluene sulfonic acid, phosphoric acid or polyphosphoric acids, silyl esters of strong acids, such as trialkyl chlorosilanes, dialkyl dichlorosilanes, alkyl trichlorosilanes, tetrachlorosilane, trialkyl silylsulfonic acids, trialkyl silyl-p-toluene sulfonates, bis-trialkyl silylsulfate and trialkyl silylphosphoric acid esters.

The amount of either stabilizer used to stabilize the electron deficient olefin prepared by the inventive processes is well known to those of ordinary skill in the art, and may be varied depending on the properties of the resulting composition made from the so formed electron deficient olefin.

The following examples are intended to illustrate but in no way limit the present invention.

EXAMPLES

Imine Formation

N-Methylidenemethylamine was prepared by mixing paraformaldehyde and an aqueous solution of methylamine (40%) with stirring at room temperature for a period of time of 2 hours. The reaction product was extracted with dichloromethane and dried. The reaction product was identified by $^1$H NMR to be a cyclic trimer.

N-Methylene-tertiary butylamine was prepared by adding tertiary butylamine (1 eq) portionwise to paraformaldehyde (1 eq) over a period of time of 30 minutes, with stirring and cooling to maintain the temperature close to room temperature. After addition, stirring was continued for a further period of time of 30 minutes at room temperature. Stirring was discontinued and the mixture separated into a pale light oily organic layer and an aqueous layer. The organic layer was separated and dried, and then purified by distillation.

N-Methylidenepropylamine was prepared following the same procedure described in the previous paragraph, replacing tertiary butylamine with propylamine.

N-Methylideneaniline was prepared by mixing paraformaldehyde and aniline in chloroform at room temperature for a period of time of 2 hours and then heating at a temperature of 50° C. for a period of time of 3 hours.

The imines formed in paragraphs [0066]-[0069] above were characterised by $^1$N NMR; for N-methylidenemethylamine and N-methylene-tertiary butylamine, the $^1$H NMR spectra show monomeric imine and trimeric forms when run in deuterated chloroform as explained in R. J. Vijin et al., *Synthesis*, 573 (1994).

Iminium Salt Formation

In a screw-capped test-tube, N-methylidene-tertiary butylamine from paragraph [0067] above (0.43 g, 5 mmol) was dissolved in deuterated chloroform (2 mls) under stirring and cooling to a temperature of 0° C. under anhydrous conditions. Methane sulfonic acid and sulfuric acid were added slowly to give an excess of acid and ensure conversion of imine to iminium salts. The reaction was observed to be exothermic.

Reaction of Iminium Salts with Methylene Compounds Bearing Electron Withdrawing Groups Ethyl cyanoacetate (0.53 g, 5 mmol) was added directly to the solution of iminium salt described above in paragraph [0074] above, at room temperature with stirring. The reaction mixture was further stirred and heated to temperature of 70° C. A 60% yield of ethyl-2-cyanoacrylate monomer was observed to have resulted after a period of time of 1 hour and a 64% yield after a period of time of 3 hours at that temperature as measured by internal referencing using $^1$H NMR.

In alternative syntheses, the following procedures were followed:

In the first procedure, the reaction was carried out in a screw-capped test-tube previously washed with acid and then dried. Tert-butylimine (0.43 g, 5 mmol) was dissolved in deuterated chloroform (2 ml) under stirring and cooled to a temperature of 0° C. with an ice bath. Methane sulphonic acid (0.23 g, 2.4 mmol) and sulphuric acid (0.33 g, 3.4 mmol) were slowly added to this solution. Ethyl cyanoacetate (0.53 ml, 5 mmol) was added dropwise at room temperature and the reaction was stirred at a temperature of 70° C. for a period of time of 3 hours.

The upper layer which separated over time was removed by Pasteur pipette. To the lower organic layer was added dropwise at room temperature a solution of iminium salt preformed from tert-butylimine (0.22 g, 2.5 mmol), methane sulphonic acid (0.12 g, 1.2 mmol), and sulphuric acid (0.17 g, 1.7 mmol), all of which was dissolved in 1 ml deuterated chloroform. The resulting mixture was stirred at a temperature of 70° C. for a period of time of 1.5 hours.

An aliquot of the reaction mixture was examined by $^1$H NMR and the yield of ethyl-2-cyanoacrylate was estimated to be in the range of about 75-80%.

In the second procedure, the reaction was carried out in a screw-capped test-tube, again previously washed with acid. Tert-butylimine (0.28 g, 3.3 mmol) was dissolved in deuterated chloroform (2 ml) under stirring and cooled to a temperature of 0° C. with an ice bath. Methane sulphonic acid (0.15 g, 1.6 mmol) and sulphuric acid (0.22 g, 2.27 mmol) were slowly added to this solution. Ethyl cyanoacetate (0.53 ml, 5 mmol) was added dropwise at room temperature and the reaction was stirred at a temperature of 70° C. for a period of time of 3 hours.

As before, the upper organic layer was removed by Pasteur pipette. To the lower organic layer was added dropwise at room temperature a solution of iminium salt preformed from tert-butylimine (0.28 g, 3.3 mmol), methane sulphonic acid (0.15 g, 1.6 mmol), sulphuric acid (0.22 g, 2.27 mmol), all of which was dissolved in 1 ml deuterated chloroform. The reaction was allowed to stir at a temperature of 70° C. for a period of 1.5 hours.

An aliquot of the reaction mixture was examined by $^1$H NMR and the yield of ethyl-2-cyanoacrylate was estimated to be about 70%.

Significantly, in each of these procedures, no oligomer or polymer was observed by $^1$H NMR analysis to have formed, which is surprising because the so-formed monomer is reactive under conventional base-catalyzed Knoevenagel conditions the monomer polymerizes and which must subsequently cracked to yield the monomer. Furthermore, $^1$H NMR showed that some unreacted ethyl cyanoacetate remained in solution ready for further conversion directly to monomer.

After removal of solvent, the glassware (previously acid washed) was reconfigured for vacuum distillation and one drop of methane sulfonic acid was placed in receiver flasks. Only ethyl cyanoacetate and ethyl-2-cyanoacrylate monomer distilled over and were collected in the liquid state. No polymer was observed to have formed at any time during the operation.

Reaction of Eschenmoser's Salt with Methylene Compounds Bearing Electron Withdrawing Groups Eschenmoser's (iodide) salt was employed as a commercially available iminium salt. When this salt was mixed into deuterated chloroform, the salt was observed to be scarcely soluble at room temperature. However, when MeSO$_3$H and H$_2$SO$_4$ were added, the colour changed becoming dark brown and the solubility increased. After heating in the presence of added ethyl cyanoacetate on an equimolar basis at a temperature of 70° C. for a period of time of 3 hours, the reaction produced monomeric cyanoacrylate, as evidenced by direct $^1$N NMR analysis.

Treatment of Removed Upper Phase

To the upper layer described above in paragraph [0078], sodium hydroxide is added to regenerate tert-butylamine. The latter may be reused to make electron deficient olefins through the use of iminium salts.

What is claimed is:

1. A process for the preparation of a reactive electron deficient olefin, steps of which comprise
    (a) providing an iminium salt prepared from an imine made as a reaction product of a primary amine and an aldehyde compound and a compound containing a methylene linkage having at least one electron withdrawing substituent attached thereto, wherein the electron withdrawing substituent is selected from the group consisting of nitrite, carboxylic acids, carboxylic esters, sulphonic acids, ketones and nitro;
    (b) reacting the iminium salt and the compound under appropriate conditions and for a time sufficient to yield a reactive electron deficient olefin and an ammonium salt;
    (c) separating the so formed reactive electron deficient olefin to yield the reactive electron deficient olefin;
    (d) contacting that which remains from step (c) with alkali to generate the primary amine; and
    (e) optionally separating the primary amine formed in step (d); and
    (f) optionally contacting the primary amine formed in step (d) with a carbonyl-containing compound under appropriate conditions and for a time sufficient to yield an imine; and
    (g) optionally contacting the imine formed in step (f) with an acid under appropriate conditions and for a time sufficient to yield an iminium salt.

2. The process of claim 1, further comprising the steps of repeating steps (a) through (g).

3. A process for the preparation of a 2-cyanoacrylate ester, steps of which comprise
    (a) providing as reactants a mixture of formaldehyde or a source thereofof, and an amine to form an imine;
    (b) reacting the imine under appropriate conditions and for a time sufficient to yield an iminium salt;
    (c) providing an alkyl cyanoacetate and reacting the iminium salt from step (b) therewith;
    (d) separating from the mixture the so-formed 2-cyanoacrylate ester to yield 2-cyanoacrylate ester substantially free from reactants;
    (e) contacting that which remains from step (d) with alkali to generate an amine; and
    (f) optionally separating the amine formed in step (e); and
    (g) optionally contacting the amine formed in step (e) with a carbonyl-containing compound under appropriate conditions and for a time sufficient to yield an imine; and
    (h) optionally contacting the imine formed in step (g) with an acid under appropriate conditions and for a time sufficient to yield an iminium salt.

4. The process of claim 3, further comprising the steps of repeating steps (a) through (h).

5. The process of claim 1, wherein the process is conducted without any added catalyst.

6. A process for the preparation of a reactive electron deficient olefin, steps of which comprise
   (a) providing an iminium salt and a compound containing a methylene linkage having at least one electron withdrawing substituent attached thereto, wherein the electron withdrawing substituent is selected from the group consisting of nitrile, carboxylic acids, carboxylic esters, sulphonic acids, ketones and nitro;
   (b) reacting the iminium salt and the compound under appropriate conditions and for a time sufficient to yield a reactive electron deficient olefin and an ammonium salt;
   (c) separating the so formed reactive electron deficient olefin to yield the reactive electron deficient olefin;
   (d) contacting that which remains from step (c) with alkali to generate an amine; and
   (e) optionally separating the amine formed in step (d); and
   (f) optionally contacting the amine formed in step (d) with a carbonyl-containing compound under appropriate conditions and for a time sufficient to yield an imine; and
   (g) optionally contacting the imine formed in step (f) with an acid under appropriate conditions and for a time sufficient to yield an iminium salt, wherein the electron deficient olefin is a cyanoacrylate.

7. A process for the preparation of a reactive electron deficient olefin, steps of which comprise
   (a) providing an iminium salt and a compound containing a methylene linkage having at least one electron withdrawing substituent attached thereto, wherein the electron withdrawing substituent is selected from the group consisting of nitrile, carboxylic acids, carboxylic esters, sulphonic acids, ketones and nitro;
   (b) reacting the iminium salt and the compound under appropriate conditions and for a time sufficient to yield a reactive electron deficient olefin and an ammonium salt;
   (c) separating the so formed reactive electron deficient olefin to yield the reactive electron deficient olefin;
   (d) contacting that which remains from step (c) with alkali to generate an amine; and
   (e) optionally separating the amine formed in step (d); and
   (f) optionally contacting the amine formed in step (d) with a carbonyl-containing compound under appropriate conditions and for a time sufficient to yield an imine; and
   (g) optionally contacting the imine formed in step (f) with an acid under appropriate conditions and for a time sufficient to yield an iminium salt, wherein the compound containing a methylene linkage having at least one electron withdrawing substituent attached thereto is an ester of cyanoacetic acid.

8. The process of claim 1, wherein the carbonyl-containing compound is an aldehyde compound.

9. A process for the preparation of a reactive electron deficient olefin, steps of which comprise
   (a) providing an iminium salt and a compound containing a methylene linkage having at least one electron withdrawing substituent attached thereto, wherein the electron withdrawing substituent is selected from the group consisting of nitrile, carboxylic acids, carboxylic esters, sulphonic acids, ketones and nitro;
   (b) reacting the iminium salt and the compound under appropriate conditions and for a time sufficient to yield a reactive electron deficient olefin and an ammonium salt;
   (c) separating the so formed reactive electron deficient olefin to yield the reactive electron deficient olefin;
   (d) contacting that which remains from step (c) with alkali to generate an amine; and
   (e) optionally separating the amine formed in step (d); and
   (f) optionally contacting the amine formed in step (d) with a carbonyl-containing compound under appropriate conditions and for a time sufficient to yield an imine; and
   (g) optionally contacting the imine formed in step (f) with an acid under appropriate conditions and for a time sufficient to yield an iminium salt, wherein the electron deficient olefin is a member selected from the group consisting of biscyanoacrylate, biscyanopentadienoate and a bis-alkylene derived from dimalonates.

10. The process of claim 1, wherein the electron deficient olefin is a compound having one end terminating with a cyanoacrylate, cyanopentadienoate, or alkylene derived from dimalonate and another end terminating with a group selected from the group consisting of branched and unbranched alkyl esters, esters containing aromatics and heterocylic nuclei, acrylates, cyanoacrylates, siloxanes, blocked and unblocked isocyanates, anhydrides, silanes, vinyls, and acetylenes.

11. The process of claim 6, wherein the electron deficient olefin is a 2-cyanoacrylate.

12. The process of claim 11, wherein the 2-cyanoacrylates are selected from the group consisting of methyl, ethyl, n-propyl, i-propyl, propargyl, n-butyl, i-butyl, n-pentyl, n-hexyl, 2-ethylhexyl, n-octyl, n-nonyl, oxononyl, n-decyl, n-dodecyl, allyl, ethynyl, 2-butenyl, cyclohexyl, phenyl, phenethyl, tetrahydrofurfuryl, chloroethyl, 2,2,2-trifluoroethyl, hexafluoroisopropyl, methoxymethyl, methoxyethyl, methoxybutyl, ethoxyethyl, propoxyethyl, butoxymethyl, butoxyethyl and dimethylsiloxane esters of 2-cyanoacrylic acid.

13. A process for using iminium salts to prepare reactive electron deficient olefins, the steps of which comprise
   (a) providing an iminium salt prepared from an imine made as a reaction product of a primary amine and an aldehyde compound and a compound containing a methylene linkage having at least one electron withdrawing substituent attached thereto, wherein the electron withdrawing substituent is selected from the group consisting of nitrile, carboxylic acids, carboxylic esters, sulphonic acids, ketones and nitro;
   (b) reacting the iminium salt and the compound under appropriate conditions and for a time sufficient to yield a reactive electron deficient olefin;
   (c) separating from the mixture the so formed reactive electron deficient olefin to yield the reactive electron deficient olefin;
   (d) contacting that which remains from step (c) with alkali to generate the primary amine; and
   (e) optionally separating the primary amine formed in step (d); and
   (f) optionally contacting the primary amine formed in step (d) with a carbonyl-containing compound under appropriate conditions and for a time sufficient to yield an imine; and
   (g) optionally contacting the imine formed in step (f) with an acid under appropriate conditions and for a time sufficient to yield an iminium salt.

14. The process of claim 13, further comprising the steps of repeating steps (a) through (g).

15. The process of claim 1, wherein the so formed reactive electron deficient olefin is substantially free from the iminium salt and the compound.

16. The process of claim 1, wherein the so formed reactive electron deficient olefin is substantially free from the carbonyl-containing compound, the primary amine, the iminium salt and the compound.

17. The process of claim 3, wherein the iminium salt is represented by:

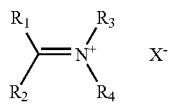

wherein $R_1$, $R_2$, $R_3$ are each H; $R_4$ is an alkyl; X is a member selected from the group consisting of $SO_3CH_3$, $0.5(SO_4^{2-})$, $HSO_4^-$ or mixtures thereof.

18. A process for the preparation of a reactive electron deficient olefin, steps of which comprise
(a) providing an iminium salt and a compound containing a methylene linkage having at least one electron withdrawing substituent attached thereto, wherein the electron withdrawing substituent is selected from the group consisting of nitrite, carboxylic acids, carboxylic esters, sulphonic acids, ketones and nitro;
(b) reacting the iminium salt and the compound under appropriate conditions and for a time sufficient to yield a reactive electron deficient olefin and an ammonium salt;
(c) separating the so formed reactive electron deficient olefin to yield the reactive electron deficient olefin;
(d) contacting that which remains from step (c) with alkali to generate an amine; and
(e) optionally separating the amine formed in step (d); and
(f) optionally contacting the amine formed in step (d) with a carbonyl-containing compound under appropriate conditions and for a time sufficient to yield an imine; and
(g) optionally contacting the imine formed in step (f) with an acid under appropriate conditions and for a time sufficient to yield an iminium salt, wherein the iminium salt is prepared from imines selected from the group consisting of N-methylidene-tertiary butylamine, N-methylideneaniline, N-methylidenemethylamine and N-methylidenepropylamine.

19. The process of claim 3, wherein the iminium salt is represented by:

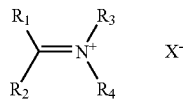

wherein:
A. $R_1$ is $CH_2=CH$, $R_2$ and $R_3$ are each H, $R_4$ is alkyl, and X is a member selected from the group consisting of $SO_3CH_3$, $0.5(SO_4^{2-})$ or mixtures of both anions, $PF_6$, $BF_4$, $AsF_6$, $SbF_6$, $Tf_2N$, $(CN)_2N$, triflate, camphorsulfonate, saccharinate, acesulfamate, $MF_6$, wherein M is Nb or Ta, nitrate, $CF_3CO_2$, halide, phosphate, and perchlorate;
B. $R_1$ and $R_2$ are each $CH_2=CH$, $R_3$ is H, $R_4$ is alkyl, and X is a member selected from the group consisting of $SO_3CH_3$, $0.5(SO_4^{2-})$, mixtures of both anions, $PF_6$, $BF_4$, $AsF_6$, $SbF_6$, $Tf_2N$, $(CN)_2N$, triflate, camphorsulfonate, saccharinate, acesulfamate, $MF_6$, wherein M is Nb or Ta, nitrate, $CF_3CO_2$, halide, phosphate, and perchlorate;
C. $R_1$ is H or $CH_2=CH$, $R_2$ is $R_1C=N^+(R_3)(R_4)X^-$, $R_3$ is H, $R_4$ is alkyl, and X is a member selected from the group consisting of $SO_3CH_3$, $0.5(SO_4^{2-})$ or mixtures of both anions, $PF_6$, $BF_4$, $AsF_6$, $SbF_6$, $Tf_2N$, $(CN)_2N$, triflate, camphorsulfonate, saccharinate, acesulfamate, $MF_6$, wherein M is Nb or Ta, nitrate, $CF_3CO_2$, halide, phosphate, and perchlorate;
D. $R_1$ and $R_2$ are each independently selected from H or $CH_2=CH$, $R_3$ and $R_4$ are each independently selected from alkyl groups or aromatic groups, X is a member selected from the group consisting of $SO_3CH_3$, $0.5(SO_4^{2-})$ or mixtures of both anions, $PF_6$, $BF_4$, $AsF_6$, $SbF_6$, $Tf_2N$, $(CN)_2N$, triflate, camphorsulfonate, saccharinate, acesulfamate, $MF_6$, wherein M is Nb or Ta, nitrate, $CF_3CO_2$, halide, phosphate, and perchlorate;
E. $R_1$ is H or $CH_2=CH$, $R_2$ is $R_1C=N^+(R_3)(R_4)X^-$, $R_3$ and $R_4$ are each independently selected from alkyl groups or aromatic groups, X is a member selected from the group consisting of $SO_3CH_3$, $0.5(SO_4^{2-})$ or mixtures of both anions, $PF_6$, $BF_4$, $AsF_6$, $SbF_6$, $Tf_2N$, $(CN)_2N$, triflate, camphorsulfonate, saccharinate, acesulfamate, $MF_6$, wherein M is Nb or Ta, nitrate, $CF_3CO_2$, halide, phosphate, and perchlorate;
F. $R_1$ and $R_2$ are each independently selected from H or $CH_2=CH$, $R_3$ is H, $R_4$ is OH, OR, wherein R is an alkyl group, aromatic group, or a carboxy group, and X is a member selected from the group consisting of $SO_3CH_3$, $0.5(SO_4^{2-})$ or mixtures of both anions, $PF_6$, $BF_4$, $AsF_6$, $SbF_6$, $Tf_2N$, $(CN)_2N$, triflate, camphorsulfonate, saccharinate, acesulfamate, $MF_6$, wherein M is Nb or Ta, nitrate, $CF_3CO_2$, halide, phosphate, and perchlorate;
G. $R_1$ is selected from H or $CH_2=CH$, $R_2$ is $R_1C=N^+(R_3)(R_4)X^-$, $R_3$ is H, $R_4$ is OH, OR, wherein R is an alkyl group, aromatic group, or a carboxy group, and X is a member selected from the group consisting of $SO_3CH_3$, $0.5(SO_4^{2-})$ or mixtures of both anions, $PF_6$, $BF_4$, $AsF_6$, $SbF_6$, $Tf_2N$, $(CN)_2N$, triflate, camphorsulfonate, saccharinate, acesulfamate, $MF_6$, wherein M is Nb or Ta, nitrate, $CF_3CO_2$, halide, phosphate, and perchlorate; or
H. $R_1$ and $R_2$ are each is selected from H or $CH_2=CH$, $R_3$ is selected from alkyl groups or aromatic groups, $R_4$ is selected from OH, OR, wherein R is an alkyl group, aromatic group, or a carboxy group, X is a member selected from the group consisting of $SO_3CH_3$, $0.5(SO_4^{2-})$ or mixtures of both anions, $PF_6$, $BF_4$, $AsF_6$, $SbF_6$, $Tf_2N$, $(CN)_2N$, triflate, camphorsulfonate, saccharinate, acesulfamate, $MF_6$, wherein M is Nb or Ta, nitrate, $CF_3CO_2$, halide, phosphate, and perchlorate.

20. The process of claim 8, wherein the aldehyde compound is a member selected from the group consisting of paraformaldeyde, formalin, and 1,3,5-trioxan.

21. The process of claim 1, wherein the iminium salt is formed from an imine made as a reaction product of a primary amine attached to a tertiary carbon and formaldehyde or a source thereof.

22. The process of claim 13, wherein the iminium salt is formed from an imine made as a reaction product of a primary amine attached to a tertiary carbon and formaldehyde or a source thereof.

23. The process of claim 1, wherein the aldehyde compound is an aldehyde or a source of an aldehyde.

24. The process of claim 13, wherein the aldehyde compound is an aldehyde or a source of an aldehyde.

* * * * *